United States Patent [19]

Sättler et al.

[11] Patent Number: 4,806,238

[45] Date of Patent: * Feb. 21, 1989

[54] CHROMATOGRAPHY COLUMN

[75] Inventors: Günther Sättler, Reinheim; Günter Hauke, Mühltal, both of Fed. Rep. of Germany

[73] Assignee: Merck Patent Gesellschaft mit Beschrankter Haftung, Darmstadt, Fed. Rep. of Germany

[ * ] Notice: The portion of the term of this patent subsequent to Apr. 12, 2005 has been disclaimed.

[21] Appl. No.: 122,815

[22] Filed: Nov. 19, 1987

Related U.S. Application Data

[63] Continuation-in-part of Ser. No. 869,549, Jun. 2, 1986, Pat. No. 4,737,284.

[30] Foreign Application Priority Data

Jun. 6, 1985 [DE] Fed. Rep. of Germany ....... 3519725
Nov. 20, 1986 [DE] Fed. Rep. of Germany ....... 3639692

[51] Int. Cl.$^4$ .............................................. B01D 15/08
[52] U.S. Cl. .................................. 210/198.2; 55/386; 285/393
[58] Field of Search ...................... 210/198.2; 55/386; 285/356, 387, 388, 393

[56] References Cited

U.S. PATENT DOCUMENTS

| Re. 31,974 | 8/1985 | Brownlee | 55/386 |
| 944,877 | 12/1909 | Koschinski | 285/388 |
| 3,298,160 | 1/1967 | Hoffman | 55/386 |
| 3,488,073 | 1/1970 | Wold | 285/388 |
| 3,679,237 | 7/1972 | De Angelis | 210/198.2 |
| 3,763,879 | 10/1973 | Jaworek | 210/198.2 |
| 3,855,130 | 12/1974 | Randau | 55/386 |
| 4,050,722 | 9/1977 | Berger | 285/388 |
| 4,070,284 | 1/1978 | Fujita | 210/198.2 |
| 4,343,496 | 8/1982 | Petranto | 285/387 |
| 4,524,998 | 6/1985 | Brisco | 285/388 |
| 4,551,249 | 11/1985 | Shackelford | 210/198.2 |
| 4,565,632 | 1/1986 | Hatch | 55/386 |

FOREIGN PATENT DOCUMENTS

| 2930962 | 2/1981 | Fed. Rep. of Germany ... 210/198.2 |
| 3021306 | 12/1981 | Fed. Rep. of Germany ... 210/198.2 |
| 3143075 | 5/1983 | Fed. Rep. of Germany ... 210/198.2 |

*Primary Examiner*—Ernest G. Therkorn
*Attorney, Agent, or Firm*—Millen & White

[57] ABSTRACT

The invention relates to a chromatography column consisting of a metal tube which is filled with a sorbent and is provided with distribution elements and sealing elements at both ends. A screw connection for connecting capillaries which consists of at least one support nut attached to the column tube and a union nut are provided. The support nut is supported against two removable collar half-shells and can thus be removed from the column tube when the union nut is unscrewed.

4 Claims, 1 Drawing Sheet

CHROMATOGRAPHY COLUMN

This application is a continuation-in-part of U.S. patent application Ser. No. 869,549 filed June 2, 1986, now U.S. Pat. No. 4,737,284.

BACKGROUND OF THE INVENTION

The invention relates to a chromatography column comprising a metal tube which is filled with a sorbent and is provided with distribution and sealing elements at both ends. A screw connection which consists of at least one support nut is attached to the column tube and a union nut for connection to capillaries is retained by the screw connector.

Numerous columns for chromatography are in use. These columns usually have, on both ends, an external thread or a support nut with an internal or external thread, so that capillary connections for feeding and removing eluent can be attached by a threaded stopper or a union nut.

Column cartridges have recently become increasingly available which do not have a screw connection, but are clamped either in a cartridge holder, as disclosed for example, in German Offenlegungsschrift No. 2,930,962, German Offenlegungsschrift No. 3,021,306 and U.S. Pat. No. 4,283,280, or inserted in a column clamping device in accordance with German Offenlegungsschrift No. 3,143,075.

For the supplier who wishes to supply his customers with both column cartridges and with columns with a reducing screw connection, considerable expense is incurred because of the double production lines and duplicate stocking. Accordingly, there is a need for columns which can be used both as cartridge columns and as columns with reducing screw connections.

It has been found that the problem can be solved by providing a removable screw connection on a column cartridge, allowing the column to be used either as a cartridge-type column or as a complete column.

In applicants' parent application, U.S. patent application Ser. No. 869,549, now U.S. Pat. No. 4,737,384, a chromatography column is provided which consists of a metal tube which is filled with a sorbent and is provided with distribution elements and sealing elements at both ends. A screw connection for connecting capillaries is provided. The screw connection consists of at least one support nut attached to the column tube plus a union nut. The support nut consists of two half-shells and can therefore be removed from the column tube when the union nut is unscrewed.

SUMMARY OF THE INVENTION

It has now been found that the solution set forth in the parent application can be improved further by providing two removable collar, half-shells against which the undivided support nut is supported, rather than by dividing the support nut itself.

The invention relates to a chromatography column consisting of a metal tube which is filled with a sorbent and is provided with frits and sealing elements at both ends. A screw connection for connecting capillaries which consists of at least one support nut attached to the column tube and a union nut are provided. The support nut is supported against two removable collar half-shells and can therefore be removed from the column tube when the union nut is unscrewed.

The construction according to the invention not only has the advantage that only one version will have to be supplied for each column type but, moreover, expenditures on reducing screw connections are also considerably reduced. In fact, only one pair of screw connections is required for each column diameter. When the column is changed, it is merely necessary to replace the cartridge, whilst the screw connection can be used further. For the user, this means considerable savings in acquisition costs.

BRIEF DESCRIPTION OF THE DRAWINGS

A preferred embodiment of the column according to the invention is shown in the drawings. Since the column is preferably symmetric in construction, only one end of the column is shown in each case.

DESCRIPTION OF THE PREFERRED EMBODIMENT

Figure 1:
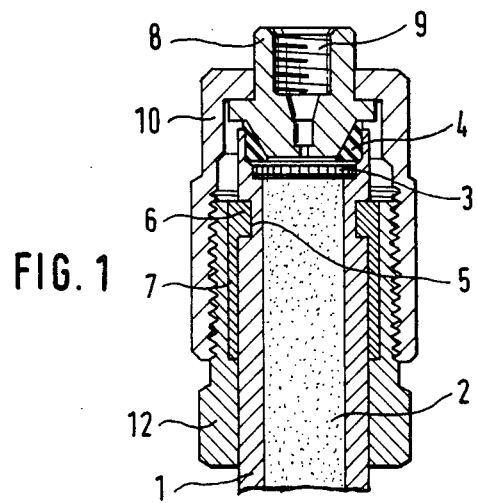
FIG. 1 shows a section through one end of the column with the screw connection attached.

The column tube 1 is usually supplied to the customer filled with a sorbent 2 and closed with a frit element 3 and a seal 4. The column tube 1 can be used in this form in a cartridge holder or column clamping device. Close to the end of the column is an annular groove 5 into which a projection 6 of the collar half-shells 7 engages. A pressure piece 8, which has a threaded bore 9, is then pressed tightly against the seal 4 with the aid of a union nut 10, which is screwed against a support nut 12.

Figure 2:
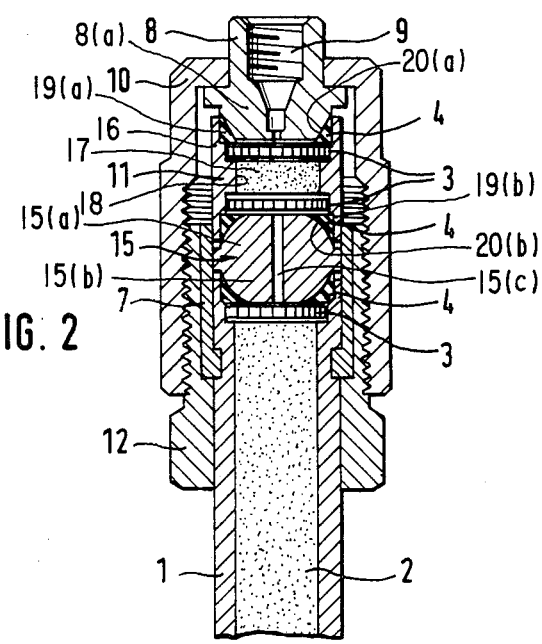
FIG. 2 shows a section through one end of the column with a precolumn inserted in the screw connection.

The cartridge column has thus become a column with a reducing screw connection by simply screwing on a few components. It is likewise easy to operate the column according to the invention with a precolumn 11. In particular, if the collar half-shells 7 are oriented as shown in FIG. 2, the support nut 12 can be pushed in the direction of the end of the column so that space for a precolumn 11 remains between the end of the column and the pressure piece 8. At its end facing the pressure piece 8, the precolumn 11 is analogous in design to the end of the column 1. The end of the precolumn 11 facing the column 1 is designed either analogously to the end of the pressure stopper 8 facing the column or analogously to the end of the column 1. In the former case, the precolumn 11 can interact as a seal directly with the end of the column 1. In the latter case, a rigid double-sealing element 15 of symmetric construction and with sealing surfaces analogous to the pressure piece 8 on both sides is inserted between the column 1 and precolumn 11 to serve in part as a spacer. The element 15 has a bore 15(a) therethrough.

Considering the arrangement of FIG. 2 more specifically, it is seen that the precolumn 11 comprises a short tube 16 having precolumn sorbent 17 therein. The short tube 16 has an external surface of a constant diameter and a stepped internal surface with a first diameter portion 18 containing the sorbent 17, second diameter portions 19(a) and 19(b) retaining the distribution elements 3 and third diameter portions 20(a) and 20(b) retaining the seals 4. The external diameter of the short tube 16 is equal to the external diameter of the column 1 so that the precolumn fits into the end of the half-shell collar 7. The opposite ends of the precolumn 11 form identical concave recepticals for receiving the convex protrusion 8(a) of the pressure piece 8 or one of the convex protrusions 15(a) and 15(b) of the rigid double sealing element 15, the other protrusion being received in the concavity defined by the seal 4 and distribution element 3 in the tube 1.

To seal the column, for example during transportation, the pressure piece 8 can be closed by a blank stopper. The column according to the invention can be manufactured in any desired length and diameter, and as already mentioned in each case only one screw connection has to be acquired for columns of the same diameter. The usual materials, such as, in particular, stainless steel, are used for the column and the screw connection. The seal 4 is preferably manufactured from inert polymers, such as, for example, PTFE, whilst the frit 3 can consist of sintered metal, ceramic or a fabric.

As a result of easy handling and inexpensive acquisition and holding of stocks, an advantageous new column for chromatography is thus provided.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A chromatography column for selective use with a precolumn and sealing elements associated with the precolumn, the chromatography column comprising:
a metal tube which is filled with a sorbent and is provided with distribution and sealing elements at both ends; end fitting assemblies each of which includes a screw connection for connecting capillaries to the end of the tube, at least one support nut attached to the tube, a union nut for threading on the support nut when the chromatography column is assembled, and a removable collar having first and second surfaces for abutment by a surface on the support nut; means on the collar for interlocking with the metal tube, the first surface on the collar being positioned closer to the interlocking means than the second surface on the collar; the collar being configured as two half-shells which upon being oriented with the second surface inboard of the first surface for abutment by the support nut configures the chromatography column as one without a precolumn and which, upon being removed and reoriented 180°, orients the first surface on the collar for abutment by the support nut; wherein the position of the support nut when abutting the collar is shifted toward the end of the tube providing space for the precolumn and associated sealing elements within the union nut.

2. A chromatography column comprising:
a metal chromatography tube having a groove therearound adjacent each end thereof, the metal tube being filled with sorbent and having internal outwardly facing shoulders at each end;
a first distribution element having first and second sides, the first distribution element seated on one of the shoulders at each end and having one side in engagement with the sorbent;
first sealing means disposed adjacent the second side of the distributor element;
a pressure member having a bore therethrough abutting the first distribution element and the first sealing means;
two half-shells each of which half-shells have an internal rib which is received in the groove in the metal chromatography tube;
a support nut surrounding the half-shells and having external threads and an internal shoulder abutting the first ends of the half-shells; and
a union nut having internal threads at one end and a shoulder at the opposite end the shoulder engaging the pressure member for urging the pressure member against the first distribution element while being threadably retained on the support nut.

3. The chromatography column of claim 2 further including:
a precolumn having a first end disposed in abutment with the first sealing means and the first distribution element and retained within the union nut, the precolumn having a second end in abutment with a second sealing means and a second distribution element;
a rigid spacer element having first and second ends, the first end abutting the second seal and the second distribution element and the second end abutting a third seal and a third distribution element positioned just inboard the end of the tube.

4. A chromatography column supply system wherein there are a plurality of chromatography columns containing sorbent and a lesser number of chromatography precolumns configured for use with some of the chromatography columns, the improvement comprising:
each chromatography column having first and second ends which are identical, the ends of each column including an external groove and having internal, outwardly facing shoulders;
two mirror image half-shells for each end of a column, each half-shell having first and second ends and having an internally projecting semicircular rib which is received in one half of the groove;
a first distribution element positioning in each column in abutment with one of the shoulders and in engagement with the sorbent in the column;
a pressure member for each column, the pressure member engaging the first distribution element if the column does not use a precolumn and engaging the precolumn directly if the column uses a precolumn;
a support nut surrounding the half-shells and having external threads and an internal shoulder abutting one of the ends of the half-shells;
union nuts for each column having internal threads for threadably engaging with the support nuts and shoulders for engaging the pressure members to urge the pressure members into abutment with the first distribution elements;
precolumns for use with some of the columns, each precolumn having a first end for abutment with the first seal means and first distribution element of a column and a second end with a second sealing means and second distribution element thereof, a portion of each of the precolumn being received between the half-shells;
rigid spacer elements for some of the columns, the rigid spacer element each having first and second ends, the first end abutting the second seal and the second distribution element and the second end abutting a third seal and a third distribution element positioned just inboard the end of a tube, whereby more than one type of chromatography column need not be stocked for use either with or without precolumns.

* * * * *